United States Patent [19]

Hermolin

[11] Patent Number: 4,499,305

[45] Date of Patent: Feb. 12, 1985

[54] PROCESS FOR PREPARATION OF CYCLOHEXYL HYDROPEROXIDE DECOMPOSITION CATALYSTS

[75] Inventor: Joshua Hermolin, Wilmington, Del.

[73] Assignee: E. I. Du Pont de Nemours and Company, Wilmington, Del.

[21] Appl. No.: 483,664

[22] Filed: Apr. 11, 1983

[51] Int. Cl.$^3$ .............................................. C07C 45/53
[52] U.S. Cl. ................................... 568/342; 568/835
[58] Field of Search ................................ 568/342, 835

[56] References Cited

U.S. PATENT DOCUMENTS

| | | | |
|---|---|---|---|
| 2,609,395 | 9/1952 | Dougherty et al. | 568/342 |
| 2,675,407 | 4/1954 | Gallo et al. | 568/342 |
| 2,851,496 | 9/1958 | Cates et al. | 568/342 |
| 3,093,686 | 6/1963 | Simon et al. | 568/342 |
| 3,404,185 | 10/1968 | Thomas et al. | 568/342 |
| 3,530,185 | 9/1970 | Pugi | 568/342 |
| 3,598,869 | 8/1971 | Volpe et al. | 568/342 |
| 3,855,307 | 12/1974 | Rony et al. | 568/342 |
| 3,917,708 | 11/1975 | Kuessner et al. | 568/342 |
| 3,923,895 | 12/1975 | Costantini et al. | 568/342 |
| 3,925,316 | 12/1975 | Brunie et al. | 568/342 |
| 3,927,105 | 12/1975 | Brunie et al. | 508/342 |
| 3,941,845 | 3/1976 | Voskuil et al. | 568/342 |
| 3,957,876 | 5/1976 | Rapoport et al. | 568/342 |
| 3,987,100 | 10/1976 | Barnette et al. | 568/342 |
| 3,987,101 | 10/1976 | Wolters et al. | 568/342 |
| 4,042,630 | 8/1977 | Wolters et al. | 568/342 |
| 4,326,084 | 4/1982 | Druliner et al. | 568/342 |
| 4,341,907 | 7/1982 | Zelonka | 568/342 |

OTHER PUBLICATIONS

*J. Prakt. Chem.* 9:173 (1959)—Hock, et al.
*Chem. Abstr.* 72:11793Y (1970)—Kamiya, et al.
*Tetrahedron* 20:1819 (1964) Ochiai.
*Inorg. Chem.* 6 (2):392 (1967) Robinson, et al.
*Russ. J. Phys. Chem.* 47(5):654 (1973) Semenchenko, et al.
*J. Org. Chem.* 42:1872 (1977)—Siegl.

*Primary Examiner*—James H. Reamer
*Attorney, Agent, or Firm*—Scott G. Hallquist

[57] ABSTRACT

An improvement in a process for decomposing mixtures of cyclohexane and cyclohexyl hydroperoxide to mixtures of cyclohexanone and cyclohexanol is disclosed. According to the improved process, stable catalyst dispersions, or solutions derived therefrom, of transition metal complexes of certain 1,3-bis(2-pyridylimino)isoindolines are formed by mixing, in cyclohexanone, cyclohexanol or mixtures of cyclohexanone, cyclohexanol and cyclohexane, cobalt, iron or manganese salts and 1,3-bis(2-pyridylimino)isoindolines.

18 Claims, 7 Drawing Figures

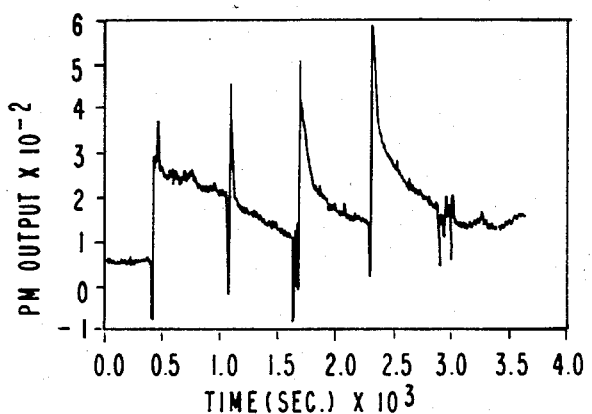
F I G. 1
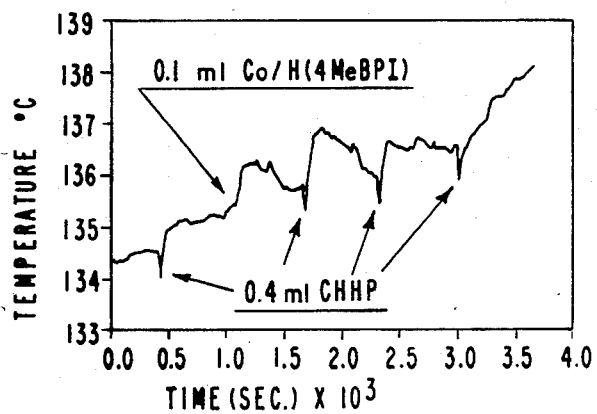
F I G. 2

PROCESS FOR PREPARATION OF CYCLOHEXYL HYDROPEROXIDE DECOMPOSITION CATALYSTS

BACKGROUND OF THE INVENTION

This invention relates to an improved process for preparing catalyst compositions for a process in which cyclohexyl hydroperoxide is decomposed to produce a mixture containing cyclohexanol and cyclohexanone. More particularly, the invention relates to an improved process for preparing stable dispersions or solutions of certain metal-ligand catalyst compositions.

Industrial processes for production of mixtures of cyclohexanol and cyclohexanone from cyclohexane are currently of considerable commercial significance, and are well described in the patent literature. In accordance with typical industrial practice, cyclohexane is oxidized, forming a reaction mixture containing cyclohexyl hydroperoxide (CHHP). The resulting CHHP is decomposed, optionally in the presence of a catalyst, to form a reaction mixture containing cyclohexanol and cyclohexanone. In the industry, such a mixture is known as a K/A (ketone/alcohol) mixture, and can be readily oxidized to produce adipic acid, which is an important reactant in processes for preparing certain condensation polymers, notably polyamides. Due to the large volumes of adipic acid consumed in these and other processes, minor improvements in processes for producing adipic acid and its precursors can provide beneficial cost advantages.

Dougherty, et al., U.S. Pat. No. 2,609,395, disclose a process for oxidation of cycloalkanes to produce cycloalkanols and cycloalkanones, wherein a cycloalkane is reacted with limited quantities of oxygen. The cycloalkane hydroperoxides thereby produced are decomposed by heating in the presence of a cycloalkane, producing cycloalkanols and cycloalkanones.

Gallo, et al., U.S. Pat. No. 2,675,407, disclose optional use of polyvalent metal catalysts in a process for oxidizing cycloalkanes. Specific catalysts disclosed include finely divided metals such as cerium, cobalt, copper, manganese and vanadium, as well as inorganic and organic salts or oxides containing such metals.

Cates, et al., U.S. Pat. No. 2,851,496, disclose a process in which cyclohexane is oxidized with molecular oxygen, optionally in the presence of a catalyst, to provide a mixture containing cyclohexanol, cyclohexanone, and CHHP. According to this process, the resulting CHHP is subsequently decomposed to K and A by heating the mixture in the presence of a bed of solid decomposition catalyst. Catalysts disclosed by this reference include solid, granular metals or metal oxides deposited upon inert supports.

Simon, et al., U.S. Pat. No. 3,093,686, disclose a process for oxidation of cyclohexane to produce mixtures of cyclohexanol and cyclohexanone, wherein oxidation is conducted in the presence of organic acid salts of cobalt, lead, manganese and chromium, which are added to a reactor as solutions in cyclohexane.

Pugi, U.S. Pat. No. 3,530,185, discloses a staged process for oxidizing cyclohexane in which a mixture of gases containing oxygen is introduced to a stream of cyclohexane at a temperature from 140° C. to 200° C. Optionally, a metal catalyst, e.g., cobalt in the form of a hydrocarbon-soluble compound, can be added to the cyclohexane stream.

Costantini, et al., U.S. Pat. No. 3,923,895, disclose a process for decomposing CHHP by heating a solution of CHHP and cyclohexane in the presence of a cyclohexane-soluble chromium derivative, which is added to a reactor column as a solution in cyclohexane.

Brunie, et al., U.S. Pat. No. 3,925,316, disclose a method of catalytically decomposing CHHP comprising heating a mixture of CHHP and cyclohexane in the presence of a soluble organic salt or chelated derivative of vanadium, molybdenum, or ruthenium.

Kuessner, et al., U.S. Pat. No. 3,917,708, disclose a process for oxidizing cycloalkanes in the presence of heavy metal salt oxidation catalysts. The anions of the heavy metal salts can be monoalkylphosphate, dialkyl phosphate, monoalkyl sulfate, alkylsulfonic acid, alkylphosphonate or dialkylphosphonate.

Brunie, et al., U.S. Pat. No. 3,927,105, disclose a cascade CHHP decomposition process employing soluble chromium derivatives, e.g., chromium carboxylates and chelated chromium derivatives, which are introduced, in solution, at the base of a reactor column.

Rapoport, et al., U.S. Pat. No. 3,957,876, describe a process for oxidizing cyclohexane in which a cyclohexane-soluble cobalt salt is employed as catalyst. Suitable catalysts disclosed include cobalt naphthenate, cobalt octoate, cobalt laurate, cobalt palmitate, cobalt stearate, cobalt linoleate and cobalt acetylacetonate.

Barnette, et al., U.S. Pat. No. 3,987,100, disclose a process for oxidizing cyclohexane in the presence of a binary catalyst system comprising prescribed amounts of cyclohexane-soluble chromium and cobalt salts, wherein CHHP formed during the reaction is decomposed to K and A in the presence of the binary catalyst.

Semenchenko, et al., *Russ. J. Phys. Chem.* 47 (5), 654 (1973) describe experiments indicating that the rate of CHHP decomposition in the presence of a cobalt stearate catalyst decreases as the reaction proceeds, presumably due to catalyst deactivation.

Catalytic decomposition of other organic hydroperoxides in the presence of certain cobalt complexes with anionic heterocyclic nitrogen-donor ligands has been reported. Hock and Kropf, *J. Prakt. Chem.* 9, 173 (1959) describe oxidation of cumene in the presence of phthalocyanine derivatives of seven different metals. Of these, cobalt phthalocyanine provided the highest overall conversion of cumene to oxidation products, the highest conversion of cumene to K/A mixture, and the lowest conversion to cumene hydroperoxide in the final mixture of products. Since acetophenone and 2-phenyl-2-propanol (K and A respectively) are known decomposition products of cumene hydroperoxide, it can be inferred that cobalt phthalocyanine was the most efficient catalyst for the cumene hydroperoxide decomposition reaction. Similarly, Kamiya, *Kogyo Kagaku Zasshi* 72(8), 1693, (1969), *Chem. Abstr.* 72, 11793Y, (1970) discloses that cobalt phthalocyanine exhibited greater catalytic activity than cobalt dodecanoate in the oxidation of cumene and autooxidation of ethylbenzene. In each case, the increased activity was attributed to "the decomposition of hydroperoxides".

Ochiai, *Tetrahedron* 20, 1819–1829 (1964) describes experiments in which cyclohexane was oxidized in the presence of cobalt, manganese and iron phthalocyanine.

Druliner, et al., U.S. Pat. No. 4,326,084, disclose an improved catalytic process for oxidizing cyclohexane to form a reaction mixture containing CHHP, and for subsequently decomposing the resulting CHHP to form a mixture containing K and A. The improvement comprises use of certain transition metal complexes of 1,3-bis(pyridylimino)isoindolines as catalysts for cyclohexane oxidation and CHHP decomposition. According to this patent, these catalysts demonstrate longer catalyst life, higher CHHP conversion to K and A, operability at lower temperatures (80°–160° C.), and reduced formation of insoluble metal-containing solids, relative to results obtained with certain cobalt (II) fatty acid salts, e.g., cobalt 2-ethylhexanoate. This patent discloses several methods for preparing the catalysts. One of the methods comprises mixing one to about two equivalents of a 1,3-bis(pyridylimino)isoindoline with a transition metal (II) salt, preferably a carboxylate, in a solvent such as benzene, chlorobenzene, or cyclohexane.

Robinson, et al., *Inorg. Chem.* 6(2), 392–394 (1967) disclose a method of preparing transition metal complexes of 1,3-bis(2-pyridylimino)isoindolines by reaction of transition metal acetate salts with 1,3-bis(2-pyridylimino)isoindolines in methanol, forming a complex exhibiting "increased solubility in organic solvents".

SUMMARY OF THE INVENTION

The present invention provides an improvement in a process for producing a mixture containing cyclohexanol and cyclohexanone, wherein cyclohexane is oxidized to provide a reaction mixture containing cyclohexyl hydroperoxide (CHHP), and wherein CHHP is subsequently decomposed in the presence of cyclohexane and a catalyst composition comprising at least one transition metal complex of cobalt, iron, or manganese and a 1,3-bis(2-pyridylimino)isoindoline ligand. The structural formula of the catalyst is set forth below:

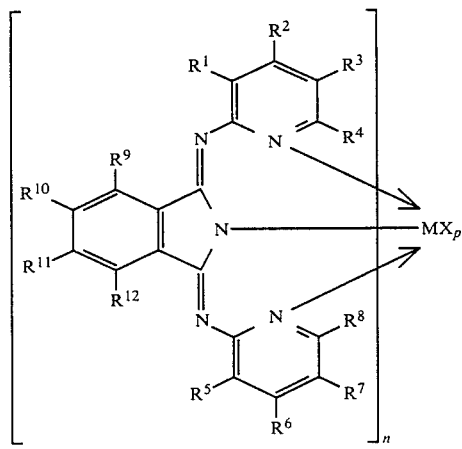

The improvement comprises forming a stable dispersion, or a solution derived therefrom, of the catalyst composition prior to introducing the catalyst composition to the reaction mixture by mixing a 1,3-bis(2-pyridylimino)isoindoline ligand of the formula

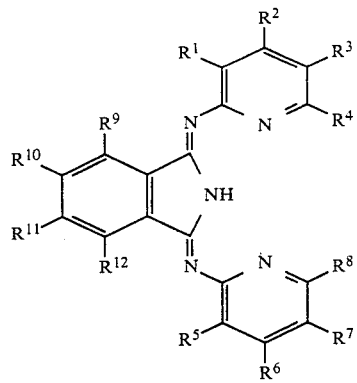

with a metal salt of formula $MX_2$ or $MX_3$ in a catalyst dispersing liquid comprising cyclohexanol, cyclohexanone, or a mixture of cyclohexanol, cyclohexanone, and from 0 to 50% cyclohexane. In the foregoing formulas, M is Co, Mn or Fe;

$R^1$, $R^2$, $R^3$, $R^5$, $R^6$ and $R^7$ are independently hydrogen, lower alkyl, lower alkoxy or alkoxyalkyl, phenyl, benzyl, or phenethyl or any two adjacent members of $R^1$ through $R^3$ and $R^5$ through $R^7$ can jointly be four CH entities of a benzene ring fused to the pyridine ring;

$R^4$ and $R^8$ are hydrogen or methyl;

$R^9$, $R^{10}$, $R^{11}$ and $R^{12}$ are independently hydrogen, lower alkyl or lower alkoxy or alkoxyalkyl or any two adjacent members of $R^9$ through $R^{12}$ can jointly be four CH entities of a benzene ring fused to the benzene ring of the isoindoline moiety; and X is an ancillary anionic ligand.

In the formula corresponding to the transition metal complex, above, the primary ligand is the entity in brackets;

n is 1 or 2; and p is 0, 1 or 2, provided that n+p is 2 or 3; with the proviso that when there are two primary ligands the values of $R^1$ through $R^{12}$ can be different for each ligand and when there are two ancillary anionic ligands, the value of X can be different.

BRIEF DESCRIPTION OF THE DRAWINGS

FIGS. 1 through 7 illustrate thermographic and chemiluminescent measurements obtained during experiments in which CHHP was decomposed using catalyst compositions prepared by the improved process of the invention, as well as other catalysts known in the art. The FIGS. correspond to Examples 1 and 2, and Comparative Examples 3 and 4, and are discussed in detail below.

DETAILED DESCRIPTION OF THE INVENTION

Figure 3:
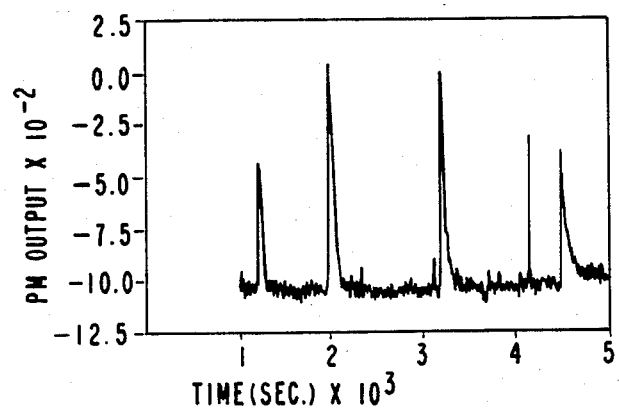
Figure 4:
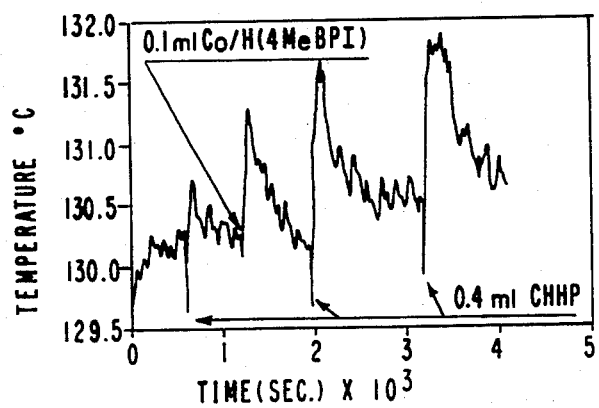

According to the present invention, an improved method for preparation of transition metal derivatives of certain 1,3-bis(2-pyridylimino)isoindolines is provided. These transition metal/ligand complexes are useful catalysts in reactions in which CHHP is decomposed to mixtures containing cyclohexanol and cyclohexanone (K and A).

Preferred catalyst complexes of the invention are those in which, in the following formula, $R^4$ and $R^8$ are hydrogen, and the remaining R groups are

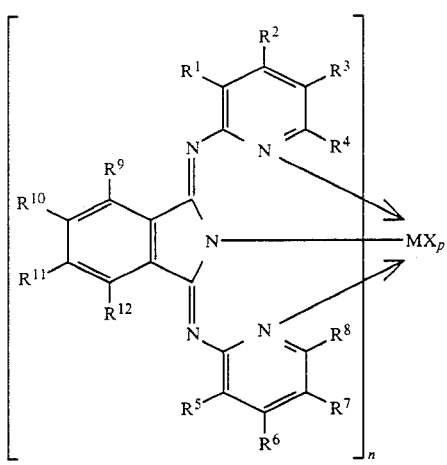

independently hydrogen or an alkyl group of 1 to 4 carbons. Preferably, M is Co. Due to availability and cost of starting materials, preferably all of $R^1$ through $R^{12}$ are hydrogen. More preferably, one of $R^1$ through $R^3$ and one of $R^5$ through $R^7$ are methyl and the remaining R groups are hydrogen. Most preferably, $R^2$ and $R^6$ are methyl and the remaining R groups are hydrogen. In the context of the present invention, "lower alkyl," "lower alkoxy," and "lower alkoxyalkyl" mean alkyl, alkoxy, and alkoxyalkyl groups having from 1 to 8 carbon atoms, respectively.

The ancillary anionic ligand, X, can be selected from various possibilities which include carboxylate groups, such as acetate, propionate, 2-ethylhexanoate, gluconate, and naphthenate; an anion of any other organic acid; hydroxide and μ-oxide ($O^{-2}/2$); dialkyl phosphate, or alkyl, aryl or alkaryl sulfonate. The nature of the ancillary anionic ligand has little direct effect on catalyst activity but can affect solubility, thereby indirectly affecting activity.

PREPARATION OF CATALYST DISPERSIONS 1,3-bis(2-pyridylimino)isoindolines can be prepared by the methods of Siegl, *J. Org. Chem.*, 42 (11), 1872 (1977). For purposes of the present invention, 1,3-bis(2-pyridylimino)isoindoline can be prepared by using calcium chloride in the method described in the section entitled "General Preparation . . . Using Alkaline Earth Salts" (page 1877 of the Siegl article).

Dispersions of transition metal 1,3-bis(2-pyridylimino)isoindoline complexes can be prepared at ambient conditions by mixing a metal carboxylate with a 1,3-bis(2-pyridylimino)isoindoline in K or A. Alternatively, plant process mixtures containing K and A can be used as catalyst dispersing liquids. For example, "steam-distilled K and A" (SDKA), a mixture obtained by steam distillation of CHHP decomposition reactor product, containing about 1 weight percent residual peroxides and about 15±2 weight percent water, can be employed. SDKA composition can vary depending upon such factors as plant process parameters and type of catalyst employed. A GC analysis of a representative SDKA sample is set forth in Table 1, below:

TABLE 1

| GC ANALYSIS OF SDKA SAMPLE | |
|---|---|
| Constituent | Approximate % (W/W) |
| Water | 17 |
| A | 56 |
| K | 24 |
| CHHP | 0.2 |
| Dicyclohexyl ether | 0.3 |
| Dicyclohexyl peroxide | 0.5 |

Where SDKA is used as a catalyst dispersing liquid, between about 0.01% and about 50% (W/W) of a suitable detergent can be added to the catalyst dispersing fluid to enhance solubilization and dispersion of the catalyst. Suitable detergents include alkylphosphate, arylphosphate, or alkylarenephosphate esters, for example, di(2-ethylhexyl)phosphate and di(n-octyl)phosphate, and sulfonates, for example, dodecylbenzenesulfonic acid and dinonylnaphthalenesulfonic acid.

Metal carboxylates used in preparing catalyst dispersions according to the process of the invention, such as Co, Fe and Mn salts of 2-ethylhexanoic acid or naphthenoic acid, are readily soluble in K, A, cyclohexane and mixtures of K and A and cyclohexane. Such metal carboxylate salt solutions can be added to solutions of 1,3-bis(2-pyridylimino)isoindolines dissolved in K or A or mixtures thereof, and mixed immediately prior to injection into a CHHP decomposition reactor. This mode of operation is denoted "in situ catalyst preparation." An alternative mode, in which metal and ligand streams are separately fed to a CHHP decomposition reactor, can also be used but results in lower catalyst activity.

PROCESS VARIABLES

Oxidation

Catalyst compositions prepared in accordance with the present invention can be employed in a cyclohexane oxidation process without regard to whether cyclohexane oxidation and CHHP decomposition are conducted in separate stages or in the same stage and regardless of whether cyclohexane oxidation is conducted in multizones, e.g., by the process disclosed in Rapaport, et al., U.S. Pat. No. 3,957,876. Except for details described herein, oxidation and decomposition steps are to be conducted in accordance with reported methods, such as those disclosed in Druliner, et al., U.S. Pat. No. 4,326,084.

CHHP Decomposition

Since CHHP is typically produced industrially as a solution in cyclohexane from catalytic oxidation of cyclohexane, a convenient and preferred solvent for the CHHP decomposition process of the invention is cyclohexane. Such a mixture can be used as received from the first step of the cyclohexane oxidation process or after some of the constituents have been removed by known processes.

The concentration of CHHP in the CHHP decomposition mixture can range from about 0.1% to about 10% by weight, preferably from about 0.5% to about 3% by weight. The catalyst concentration in the total mixture, measured as the concentration of metal cation, can be from about 0.1 to about 30 ppm, and preferably ranges from about 0.1 to 5 ppm. Typically, lower catalyst concentrations are required at higher temperatures.

The catalyst concentration of catalyst composition feedstocks prepared in accordance with the invention, measured as the concentration of metal cation in the mixtures or dispersions used as catalyst feeds, can range from about 100 to about 10,000 ppm. A preferred range of concentration is from about 500 to about 5,000 ppm. Selected amounts of these concentrated catalyst compositions can be fed to the CHHP decomposition process to achieve suitable process catalyst concentrations.

Reaction time depends upon temperature and catalyst concentration and typically ranges from about 5 to about 30 minutes. Longer times can be used, but usually no advantage results. As shown in FIGS. 1 through 7, progress of a CHHP decomposition reaction can be monitored photometrically and calorimetrically. These methods are helpful in determining an optimum process time for a given catalyst and a particular set of concentration/temperature variables. Reaction temperature for the CHHP decomposition process of the present invention can range from about 80° to 160° C. A preferred temperature range is from about 100° to about 130° C. Pressures of from about 69–2760 kPa (10–400 psi) gauge pressure are suitable, and pressures from about 276 to about 1380 kPa (40–200 psi) are preferred.

Catalyst compositions prepared in accordance with the process of the invention exhibit several advantages relative to previously disclosed CHHP decomposition catalyst preparations. For example, separately prepared Co, Fe or Mn metal complexes of 1,3-bis(2-pyridylimino)isoindolines are only slightly soluble in solvents such as cyclohexane, benzene, or other hydrocarbons. In contrast, dispersions or solutions of transition metal/1,3-bis(2-pyridylimino)isoindoline complexes or derivatives prepared according to the process of the invention are easily pumpable and remain well dispersed for relatively long periods.

Other advantages of catalyst dispersions prepared in accordance with the process of the present invention include longer lived CHHP decomposition catalyst activity, relative to a catalyst solution. In addition, preparing and storing catalyst dispersions in high concentration in K or A alleviates problems in handling large volumes of solvents. Using K or A in catalyst preparation adds nothing new or foreign to plant streams, and K or A can be fully recovered in the course of routine plant operations. Relatively inexpensive derivatives of 1,3-bis(pyridylimino)isoindoline, such as 1,3-bis(2-pyridylimino)isoindoline and 1,3-bis(3-methyl-2-pyridylimino)isoindoline, can be successfully employed as dispersed catalysts in the process of the invention, rather than more expensive but more soluble derivatives such as 1,3-bis(4-ethyl-2-pyridylimino)isoindoline or 1,3-bis(4-t-butyl-2-pyridylimino)isoindoline. Furthermore, the process of the invention eliminates the need for isolation, purification or resolution steps in preparing catalyst mixtures, and affords increased flexibility in plant operations, since changes in ligand type, metal, and mole ratios of metal to ligand can be quickly accomplished under commercial operating conditions.

The invention is further illustrated by the following preparations and examples, in which all temperatures are in degrees Celsius and all percentages are by weight unless otherwise indicated.

PREPARATIONS AND EXAMPLES

Preparations 1–8 describe methods for preparing metal catalyst dispersions or solutions representative of the invention. In the following discussion, various 1,3-bis(2-pyridylimino)isoindoline species or metal/ligand derivatives thereof have been abbreviated, as set forth below:

| Abbreviation | Ligand or Metal/Ligand Derivative |
| --- | --- |
| H(BPI) | 1;3-bis(2-pyridylimino)isoindoline |
| H(3MeBPI) | 1,3-bis(3-methyl-2-pyridylimino)-isoindoline |
| Co(3MeBPI)$_2$ | Co(II) complex of H(3MeBPI) |
| Co/H(3MeBPI) | Mixture of Co(II) derivatives of H(3MeBPI) |
| H(4MeBPI) | 1,3-bis(4-methyl-2-pyridylimino)-isoindoline |
| Co/H(4MeBPI) | Mixture of Co(II) derivatives of H(4MeBPI) |
| H(3,4'MeBPI) | 1-(3-methyl-2-pyridylimino)-3-(4-methyl-2-pyridylimino)isoindoline |
| Co/H(3,4'MeBPI) | Mixture of Co(II) derivatives of H(3,4'MeBPI) |
| H(3Me/4MeBPI) mixture | Mixture of H(3,4'MeBPI), H(3MeBPI), H(4MeBPI) |
| Co/H(3Me/4MeBPI) mixture | Mixture of Co(II) derivatives of H(3Me/4MeBPI) mixture |

Preparations 4 and 5 describe preparation of a cobalt/mixed ligand catalyst composition, which is herein designated a "Co/H(3Me/4MeBPI) mixture." This mixture consists essentially of cobalt (II) derivatives of ligand species selected from the group consisting of H(3,4'MeBPI), H(3MeBPI) and H(4MeBPI). The H(3Me/4MeBPI) mixture employed in Preparations 4 and 5, containing about 50% H(3,4'MeBPI), 25% H(3MeBPI) and 25% H(4MeBPI), was prepared by reacting 1,2-dicyanobenzene with a 50:50 mixture of 2-amino-3-methylpyridine and 2-amino-4-methylpyridine in the Siegl ligand synthesis described above.

Examples 1 and 2 describe experiments in which dispersions of transition metal complexes, prepared in accordance with the present invention, were employed as CHHP decomposition catalysts. Comparative Example 3 describes a control experiment demonstrating decomposition of CHHP catalyzed by Co(oct)$_2$ dissolved in cyclohexanone. Comparative Example 4 describes an additional control experiment demonstrating, for comparison purposes, decomposition of CHHP catalyzed by a cyclohexane solution of Co(3MeBPI)$_2$.

Cobalt (II) 2-ethylhexanoate (Co(oct)$_2$) used in the examples was obtained from the manufacturer as a mixture containing about 12.5% cobalt by weight. Cobalt concentrations were determined by atomic absorption analysis.

The apparatus used in Examples 1 through 4 was a stainless-steel pulse reactor having a volume of about 125 ml and usable at internal pressures up to about 2070 kPa (300 psi) gauge pressure. The reactor had a pressure-relief valve to insure that allowable pressure was not exceeded and was equipped with a side-arm with a septum for injection of liquid from a hypodermic syringe. Liquid contents (typically about 25 ml) in the apparatus could be stirred by an external magnetic drive. Heating was provided by partial immersion in a fluidized bed regulated by a proportional heater control. Temperatures were measured with a platinum resistance thermometer using digital temperature display and analog output.

The reactor was also equipped with a side-arm light probe for observing chemiluminescence produced during CHHP decomposition. The light thus produced passed through a flexible light guide to a photomultiplier (PM). The current output from the photomultiplier (typically 0.1–100 nA) was converted to a voltage by an electrometer amplifier with good linearity and low noise characteristics. Voltages representing the temperature (T) and the chemiluminescent light intensity (I) were passed through an analog/digital converter and stored on disks and magnetic tapes in a computer system.

Viscosity measurements of certain samples were determined by procedures described by ASTM methods D2512-annex A1 and D445 (for Newtonian fluids), using a semimicro glass capillary viscometer in a thermostated bath at 25.0°.

PREPARATION 1

Preparation and Characteristics of Co/H(4MeBPI)(1:1) Dispersion in K 0.2 g Co(oct)$_2$ (12.5% Co, 0.42 mmol) was added to 10 g cyclohexanone (K). Upon gentle stirring, the resulting mixture formed a clear, blue solution. 0.19 g (0.58 mmol) H(4MeBPI) was added, and the resulting solution turned brown in color. After shaking for about 5 minutes at about 25°, a dispersion of fine brown particles formed in the brown solution. Following storage for at least 180 days, no precipitation or other physical change was observed in the dispersion. Centrifugation at about 1000 rpm for about 10 minutes in an International Model CL 1588B clinical centrifuge also did not affect the physical characteristics of the dispersion.

To evaluate pumpability characteristics, the dispersion was continuously pumped through a section of 1.59 mm (0.0625 in) I.D. stainless steel tubing for a period of about 408 hours, using a positive displacement pump and a glass beaker as a reservoir. No changes in the physical characteristics of the dispersion were observed. Filtration of the dispersion separated the fine particles of the dispersion from the solution. UV-visible spectroscopic analysis of the resulting filtrate indicated that about 5% of the available metal-ligand complex was dissolved in the K.

PREPARATION 2

Preparation of Co/H(4MeBPI)(1:1) Dispersion in SDKA

The procedure described in Preparation 1 was substantially repeated using steam-distilled K and A effluent (SDKA) from an industrial CHHP reactor in place of K. 0.13 g (0.41 mmol) H(4MeBPI) was added to a solution of 0.20 g (0.42 mmol) Co(oct)$_2$ in 10 g SDKA, providing a dispersion of fine brown-red particles.

PREPARATION 3

Preparation and Dilution of Co/H(4MeBPI)(0.5:1) Dispersion in SDKA

The procedure described in Preparation 2 was substantially repeated, using 0.3 g (0.92 mmol) H(4MeBPI). The resulting brown/red dispersion was diluted tenfold in SDKA, providing a red solution containing 250 ppm Co.

PREPARATION 4

Preparation of Co/H(3Me/4MeBPI) mixture (1:1) in SDKA with Addition of Di(2-ethylhexyl)phosphate Preparation 2 was substantially repeated, using 0.15 g (0.48 mmol) H(3Me/4MeBPI) mixture, providing a dispersion of fine, brown-red particles. 0.5 g di(2-ethylhexyl)phosphate was added to the dispersion at about 23°. The resulting red solution, free of suspended or dispersed solids, contained 2380 ppm Co.

PREPARATION 5

Preparation of Concentrated Co/H(3Me/4MeBPI)(1:1) Catalyst Solution in SDKA with Addition of Di(2-ethylhexyl)phosphate 0.20 g (0.42 mmol) Co(oct$_2$), 0.15 g (0.48 mmol) H(3Me/4MeBPI) mixture, 0.5 g di(2-ethylhexyl)phosphate and 1.85 g SDKA were mixed, forming a high viscosity dispersion. Following addition of an additional 0.5 g di(2-ethylhexyl)phosphate, a viscous red solution resulted (7800 ppm Co, $\rho$=0.98 g/ml; $\eta$=approximately 20 centipoise).

PREPARATION 6

Preparation of Co/H(3MeBPI)(0.5:1) Dispersion in SDKA

Preparation 2 was substantially repeated, using 0.31 g (0.94 mmol) H(3MeBPI) as ligand. A reddish-brown particulate dispersion resulted.

PREPARATION 7

Preparation of Co/H(BPI)(0.5:1) Dispersion in SDKA

Preparation 2 was substantially repeated, using 0.23 g (0.77 mmol) H(BPI) as ligand. Warming the mixture to about 60° produced a dispersion of red particles in a red solution.

PREPARATION 8

Model In-Situ Preparation of Co/H(4MeBPI)(1:1) Catalyst Composition in SDKA

Two solutions, one of metal carboxylate (0.80 g; 1.7 mmol Co(oct)$_2$), and one of ligand (0.56 g; 1.7 mmol H(4MeBPI)) were prepared, each in 40 g SDKA. Two microinjector pumps were arranged to deliver the respective solutions at a rate of 3 ml/hr into a section of 1.59 mm (0.0625 in) I.D. stainless steel tubing approximately 61 cm (24 in) in length. The tubing was connected to a section of glass capillary which, in turn, was connected to a back pressure regulator via an additional section of stainless steel tubing. The regulator was adjusted to maintain about 207 kPa (30 psi) back pressure.

A reference solution was prepared by thoroughly mixing equal volumes of the metal and ligand solutions. The pumps were operated and the olive-green metal and pale yellow ligand solutions mixed in the tubing. The resulting mixture, observed through the glass capillary, appeared as a brown-red solution. Comparison of the pump-mixed solution and the reference solution by UV-visible spectroscopy indicated that the two solutions were substantially identical.

EXAMPLE 1

Decomposition of CHHP in Cyclohexane Catalyzed by Co/H(4MeBPI)(1:1) Catalyst Dispersion in K The pulse reactor apparatus previously described was charged with about 25 ml cyclohexane, sealed, and placed in a fluidized bed heater. The temperature of the reactor was permitted to rise to about 134° over a period of about ten minutes. At this point 0.4 ml of a concentrated A/O tails solution was injected into the reactor through the injection port. "Concentrated A/O tails" refers to an effluent mixture obtained from oxidation of cyclohexane in a plant air oxidizer, followed by evaporative concentration. This mixture contains approximately 50% CHHP, as well as K, A, and certain other oxidation products. In the sequence and at the times indicated below, the following samples were injected into the reactor:

1. 24 min.: 0.1 ml of a tenfold dilution of a Co/H(-4MeBPI) dispersion in K, prepared substantially as described in Preparation 1 and containing about 250 ppm Co.
2. 31 min.: 0.4 ml 50% CHHP in A/O tails;
3. 40 min.: 0.4 ml 50% CHHP in A/O tails;
4. 50 min.: 0.4 ml 50% CHHP in A/O tails.

After an additional 10 minutes, the reactor was permitted to cool to about 23°. The reactor contents were analyzed by GC to determine the concentration of residual CHHP (glass column; SP 1220 containing 10% $H_3PO_4$; $T_1 = 50°$ (1 min); $\Delta T/\Delta t = 10°$ /min; $T_2 = 190°$ (5 min). According to this analysis, approximately 90% of the available CHHP had decomposed. Light intensity vs. time, and temperature vs. time data for this experiment are plotted in FIGS. 1 and 2, respectively. The decomposition of CHHP produces chemiluminescence, and the intensity of the light at any time is a direct measure of the rate of decomposition. In addition, CHHP decomposition is an exothermic reaction, and the progress of a given decomposition reaction can be monitored by observation of reaction mixture temperature.

EXAMPLE 2

Decomposition of CHHP in Cyclohexane Catalyzed by a Dispersion of Co/H(4MeBPI)(0.5:1) in K Example 1 was substantially repeated except that 0.1 ml of a Co/H(4MeBPI) dispersion in K containing twice as much H(4MeBPI) as the amount shown in Example 1, was used in step 1. The resulting catalyst concentration in the reactor was about 1 ppm Co. An initial temperature of about 130° was used. GC analysis revealed that 90% of the CHHP had been decomposed. Light intensity vs. time data and temperature vs. time data are shown plotted in FIGS. 3 and 4, respectively.

The light and temperature traces from Examples 1 and 2, in which Co/H(4MeBPI) dispersions were used as catalysts, (FIGS. 1, 2, 3, 4), show that the respective catalyst compositions remained active for the duration of each experiment. In contrast, corresponding light and temperature traces from Comparative Example 3 (see below), in which Co(oct)$_2$ only was used as catalyst, demonstrate a significant decrease in catalyst activity following an initial injection of CHHP.

COMPARATIVE EXAMPLE 3

Decomposition of CHHP in Cyclohexane Catalyzed by Co(oct)$_2$ Dissolved in K

Figure 5:
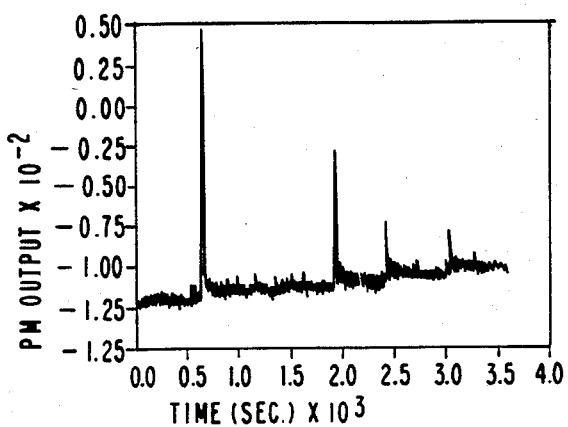
Figure 6:
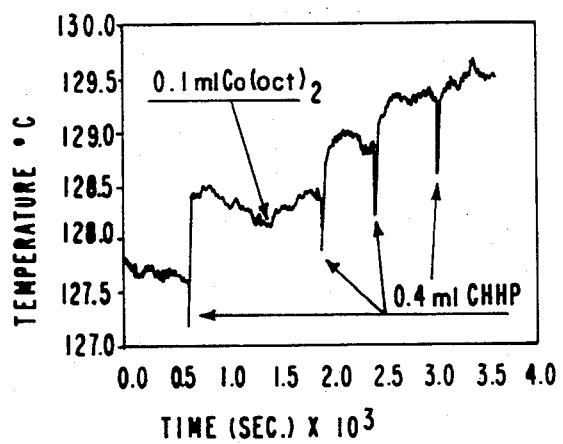
Figure 7:
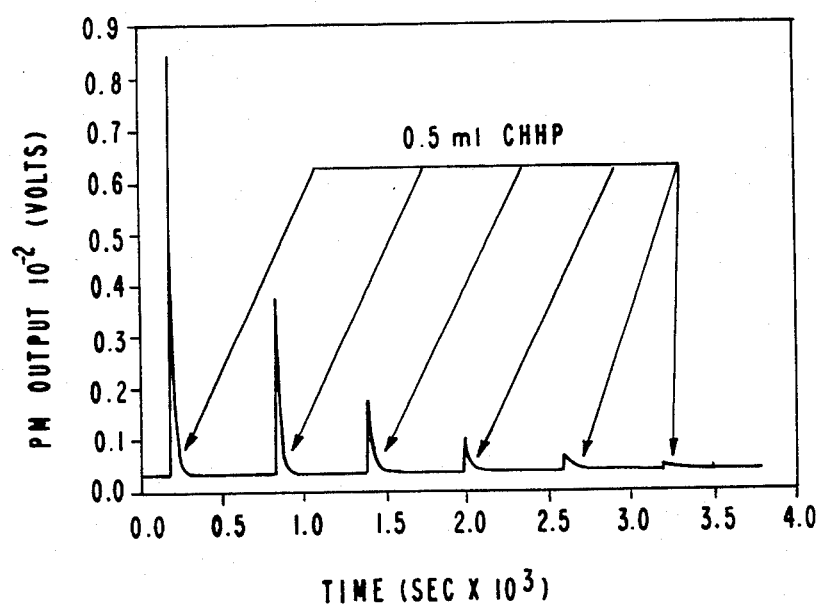

Example 1 was substantially repeated, except that 0.1 ml of Co(oct)$_2$ in K (250 ppm Co), sufficient to provide 1 ppm Co in the reaction mixture, was used as catalyst in step 1. An initial temperature of about 128° was used. GC analysis revealed that less than 50% of the CHHP had been decomposed. The light/time data and temperature/time data are shown in FIGS. 5 and 6, respectively.

COMPARATIVE EXAMPLE 4

Decomposition of CHHP in Cyclohexane Catalyzed by Co(3MeBPI)$_2$ Dissolved in Cyclohexane The pulse reactor was charged with 25 ml cyclohexane containing 8.3 mg of DBA (9,10-dibromoanthracene) added as light enhancer, sealed and placed in a fluidized bed heater. The temperature of the solution was raised to about 130° over a ten minute period. Next, 0.25 ml of a 0.24% solution of Co(3MeBPI)$_2$ in benzene was injected into the reactor (sufficient to give 2 ppm Co). Next, at intervals of 10 minutes each, a total of 6 samples of 50% CHHP in cyclohexane, 0.5 ml each, were injected into the reactor. The light intensity/time data plotted in FIG. 7 indicate that measured light intensity decreased significantly with subsequent additions of CHHP, relative to experiments in which Co/H(4MeBPI) catalyst dispersions were employed. Thus, CHHP decomposition catalyst activity is prolonged by using dispersed Co/H(BPI)-type catalyst compositions, relative to dissolved catalysts.

While the preferred embodiments of the invention are illustrated by the above, it is to be understood that the invention is not limited to the precise construction herein disclosed and that the right to all modifications coming within the scope of the appended claims is reserved.

I claim:

1. In a process for producing a mixture containing cyclohexanol and cyclohexanone, wherein cyclohexyl hydroperoxide is decomposed in a reaction mixture comprising cyclohexane and a catalytic amount of a catalyst composition consisting essentially of at least one transition metal complex having the structural formula

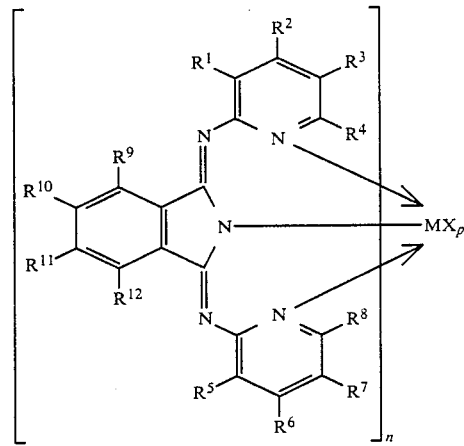

the improvement comprising forming a catalyst composition feedstock prior to introducing the catalyst composition to the reaction mixture, wherein said feedstock is a stable dispersion formed by mixing a 1,3-bis(2-pyridylimino)isoindoline ligand having the structural formula

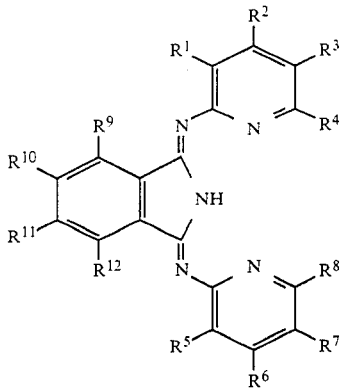

with a metal salt of formula $MX_2$ or $MX_3$ in a catalyst dispersing liquid selected from the group consisting of
(a) cyclohexanol;
(b) cyclohexanone;
(c) a mixture of cyclohexanol, cyclohexanone, and from 0–50% cyclohexane; and
(d) a plant process mixture (SDKA) obtained by steam distillation of cyclohexyl hydroperoxide decomposition reactor product, said mixture consisting essentially of cyclohexanone, cyclohexanol, water, dicylohexyl peroxide, dicyclohexyl ether, and cyclohexyl hydroperoxide; wherein
the primary ligand is the entity in brackets;
M is Co, Mn or Fe;
$R^1$, $R^2$, $R^3$, $R^5$, $R^6$ and, $R^7$ are independently hydrogen, lower alkyl, lower alkoxy, lower alkoxyalkyl, phenyl, benzyl, or phenethyl, or any two adjacent members of $R^1$ through $R^3$ and $R^6$ through $R^7$ can jointly be four CH entities of a benzene ring fused to the pyridine ring;
$R^4$ and $R^8$ are hydrogen or methyl;
$R^9$, $R^{10}$, $R^{11}$ and $R^{12}$ are independently hydrogen, lower alkyl, lower alkoxy, lower alkoxyalkyl or any two adjacent members or $R^9$ through $R^{12}$ can jointly be four CH entities of a benzene ring fused to the benzene ring of the isoindoline moiety;
X is an ancillary anionic ligand;
n is 1 or 2; and
p is 0, 1 or 2, provided that n=p is 2 or 3; with the proviso that when there are two primary ligand, the values of $R^1$ through $R^{12}$ can be different for each ligand and when there are two ancillary anionic ligands, the value of X can be different.

2. A process according to claim 1 wherein M is Co.

3. A process according to claim 2 wherein $R^4$ and $R^8$ are hydrogen, the remaining R groups are independently hydrogen or alkyl groups of 1 to 4 carbons, p is 0 or 1, and n is 2.

4. A process according to claim 3 wherein at least one of $R^1$ through $R^3$, one of $R^5$ through $R^7$, and one of $R^9$ through $R^{12}$ is hydrogen.

5. A process according to claim 4 wherein at least two of $R^1$ through $R^3$, two of $R^5$ through $R^7$, and two of $R^9$ through $R^{12}$ are hydrogen.

6. A process according to claim 5 wherein at least one of $R^1$ through $R^3$, one of $R^5$ through $R^7$, and one of $R^9$ through $R^{12}$ is methyl.

7. A process according to claim 5 wherein $R^2$ and $R^6$ are t-butyl, and each of the remaining R groups is hydrogen.

8. A process according to claim 2 wherein X is a carboxylate, phosphate, or sulfonate group.

9. A process according to claim 2 wherein the catalyst dispersing liquid is SDKA.

10. A process according to claim 9 wherein an effective solubilizing amount of a detergent is added to the stable dispersion.

11. A process according to claim 10 wherein the detergent is selected from the group consisting of alkylphosphate, arylphosphate and alkylarenephosphate esters, alkyl sulfonates and alkaryl sulfonates.

12. A process according to claim 1 wherein separate solutions of ligand and metal salt are prepared by dissolving the ligand and the metal salt in suitable solvents, and a stable dispersion of the catalyst composition is formed by mixing the separate solutions of ligand and metal salt immediately prior to injection of the catalyst composition into a cyclohexyl hydroperoxide decomposition reactor.

13. A process according to claim 1 wherein the concentration of cyclohexyl hydroperoxide in the reaction mixture is from about 0.1% to about 10% by weight.

14. A process according to claim 13 wherein the concentration of cyclohexyl hydroperoxide is from about 0.5% to about 3% by weight.

15. A process according to claim 1 wherein the concentration of catalyst composition in the reaction mixture is from about 0.1 ppm to about 30 ppm of metal by weight.

16. A process according to claim 15 wherein the concentration of catalyst composition in the reaction mixture is from about 0.1 ppm to about 5 ppm of metal by weight.

17. A process according to claim 1 wherein cyclohexyl hydroperoxide is decomposed at a temperature from about 80° C. to about 160° C., and at a pressure from about 69 kPa to about 2760 kPa.

18. A process according to claim 17 wherein cyclohexyl hydroperoxide is decomposed at a temperature from about 100° C. to about 130° C., and at a pressure from about 276 kPa to about 1380 kPa.

* * * * *